United States Patent [19]

Butler

[11] 4,149,999
[45] Apr. 17, 1979

[54] ANTISTATIC LIQUID MEDIA, AND METHOD, FOR THE CONTROLLED TRANSPORT OF MICROSCOPIC PARTICLES

[75] Inventor: John V. Butler, Newhall, Calif.

[73] Assignee: Lockheed Aircraft Corporation, Burbank, Calif.

[21] Appl. No.: 841,006

[22] Filed: Oct. 11, 1977

[51] Int. Cl.$^2$ ............................................. H01B 1/04
[52] U.S. Cl. .......................... 252/500; 260/DIG. 16; 260/DIG. 20
[58] Field of Search ............ 252/500, 8.8 AN, 8.8 AJ; 260/DIG. 16, DIG. 20

[56] References Cited

U.S. PATENT DOCUMENTS

| | | | |
|---|---|---|---|
| 2,891,878 | 6/1959 | Chamberlain | 260/DIG. 20 |
| 3,071,818 | 1/1963 | Miura et al. | 260/DIG. 20 |
| 3,324,091 | 6/1967 | Savides | 260/DIG. 20 |
| 3,674,711 | 7/1972 | Growald et al. | 252/500 |
| 3,743,608 | 7/1973 | Habu et al. | 252/500 |

OTHER PUBLICATIONS

Condensed Chemical Dictionary, (8th Ed.), Revised by Gessner G. Hawley, 1971, pp. 420, 564.

*Primary Examiner*—Benjamin R. Padgett
*Assistant Examiner*—E. Suzanne Park
*Attorney, Agent, or Firm*—Ralph M. Flygare

[57] ABSTRACT

An antistatic liquid, and method of use thereof, comprising an ionizable electroconductive polymer, an alcohol and a suitable solvent, for suppressing electrostatic charges which might otherwise develop in certain procedures relating to the manipulation and transport of microspheres, microbeads, or other microscopic particles, as well as the suppression of the reformation of polymers which might otherwise interfere with such procedures.

7 Claims, No Drawings

ANTISTATIC LIQUID MEDIA, AND METHOD, FOR THE CONTROLLED TRANSPORT OF MICROSCOPIC PARTICLES

BACKGROUND OF THE INVENTION

A number of procedures exist in a variety of industries which involve the manipulation, counting, and transfer of microscopically-sized particles. Such particles typically may range in size from approximately 0.1 micrometer to 100 micrometers or larger, and may comprise microballoons, microspheres, microbeads, dust, liquid or gas contaminants, or powders used in chemical formulations. The grading or sizing of such particles is a common and widespread industrial process. Furthermore, the counting of such particles is also required in certain test and industrial procedures. For example, it is frequently required to calibrate so-called electronic particle counters of the type used in contamination control studies, blood-cell counting, examination of hydraulic fluid contaminants, etc. The calibration of such counters is conventionally accomplished by introducing a known quantity of suitably-sized microspheres or microbeads into the counter. In other cases, a sample of the particles to be counted or graded is arranged on a microscope slide with a superimposed reticle to permit examination by microscope or by means of an optical comparator. It is found that frequently, electrostatic charges tend to cause the beads or particles to congregate into inseparable clusters on the microscope slide. Furthermore, electrostatic charges on the separating probe tend to cause the beads to disperse in many directions, or to disperse into smaller clusters. Where the particles or beads are introduced into an electronic particle counter, the beads have a tendency to stick to the bottle they are contained in and the counter walls or the conduits through which the beads must pass in the counter, as a result of the buildup of small but significant static charges therein.

The use of ionizing radiation, controlled humidity, and other well-known techniques have been attempted heretofore to suppress troublesome electrostatic charges in the handling of small particles. However, such procedures have not been altogether satisfactory, and in many instances interfere with the intended result.

BRIEF SUMMARY OF THE PRESENT INVENTION

The present invention comprises a novel and improved antistatic fluid, and related utilization methods, which may be used for the handling and transfer of microscopic particles to suppress unwanted electrostatic effects attendant thereto. In its simplest form, the carrier comprises an electroconductive aqueous solution of a cationic electrical conductive polymer and a polymer solvent comprising a trihydric alcohol mixed with a water solvent. Analogous formulations are provided for use with microbead carrier which are intended for dissolution in solvents other than water.

DETAILED DESCRIPTION OF THE PREFERRED EMBODIMENT

The preferred application of the invention is to provide a liquid medium for use as a carrier in the handling and transport of microscopic particles or beads in certain test procedures. There is described in U.S. Pat. No. 3,791,192, "Particle Standard and Calibration Method", issued Feb. 12, 1974, John V. Butler, inventor, of common assignee herewith, a particle standard comprising a plurality of microbeads which are geometrically aligned and carried in a soluble carrier matrix. As is disclosed in the aforementioned patent, it is required to dissolve the matrix carrier in order to release the microbeads into the test system or utilization apparatus. Not infrequently, the carrier solvent comprises a non-conductor such as distilled water, or a dielectric hydrocarbon solvent. As a consequence, electrostatic charges, induced in part by triboelectric effects, result in an undesired electrostatic charge being built up on the surface of the particles. These charges, being of like polarity, cause attraction with resulting clumping, or agglomeration, of the particles which interferes with their use and the desired dispersion into the system. Additionally, electrostatic charges also tend to cause the microbeads to adhere to the walls of the container or passages of the test system, or utilization apparatus.

By using the novel and improved formulation of the present invention as the solvent for dissolving the soluble carrier matrix, the buildup of electrostatic charges is precluded.

The formulation of the first embodiment comprises a water-soluble electroconductive resin, glycerol, and water in the proportions given in the example set forth hereinafter. The function of the electroconductive resin constituent is to provide a conductive coating for the microbeads which will prevent the buildup of electrostatic charges thereon. The desired electrical conductivity is brought about through ionic means rather than electronic means. The polyelectrolyte may comprise either a cationic or anionic type of polymer. A typical conductive polymeric material, suitable for use in the invention, has pendent ionizable chemical moieties in which the ionization and subsequent conductivity is dependent upon accessibility to water. The class of polymeric material selected for use does not cross-link, for to do so would interfere with the proper functioning of the invention. An example of a suitable electroconductive resin is polyvinylbenzyltrimethyl ammonium chloride. An aqueous solution of this material provides a cationic type of electroconductive polymer. In solution this material is a powerful flocculent and strongly adheres to the surface of the particles or microbeads.

The aqueous solution, in addition to providing a carrier for the microbeads through the test system, also serves to dissolve the soluble carrier matrix used to align and releasably support the beads in the manner described in the aforementioned patent. It has been found, however, that the soluble carrier matrix which typically comprises a polyvinyl alcohol (PVA) polymer, has a tendency to repolymerize. Clumps of this polymerizing material would interfere with the dispersion of the microbeads and may, for example, result in spurious counts in a particle counter which is to be calibrated by means of the microbeads. In order to aid in redissolving the PVA, the formulation of the present invention further includes a trihydric alcohol, such as glycerol. In addition to preventing repolymerization of the carrier matrix material, the humectant properties of the glycerol aid in supplying the necessary water for ionization of the polyelectrolyte. Thus, the glycerol has a synergistic property in the formulation.

As described in the aforementioned patent, the carrier matrix is made by mixing the PVA polymer in a powder form with water and then recirculating the mixture through a pumping and filtration system until the polymer is completely dissolved and free of lumps.

The solution is then formed into a film and allowed to evaporate to provide the matrix medium to carry or support the microbeads.

EXAMPLE I

The following example lists quantities sufficient for making one liter of the first embodiment of the invention:

Into a suitable (e.g., glass) container, place 100 milliliters of a 33% aqueous solution of polyvinylbenzyltrimethyl ammonium chloride (Dow XD-7036); 6 milliliters of glycerol; and, 894 milliliters of distilled water. Filter through a filter apparatus until the fluid is clean and free of agglomerates.

EXAMPLE II

The following example lists quantities sufficient for making one liter of the second embodiment of the invention:

Into a suitable container, place 100 milliliters of stearamidopropyldimethyl-β-hydroxyethylammonium dihydrogen phosphate 35% solution (Cyastat SP—American Cyanamid Co.); and 900 milliliters of methanol. Filter through a filter apparatus until the fluid is clean.

EXAMPLE III

The following example lists quantities sufficient for making one liter of the third embodiment of the invention:

Into a suitable container, place 100 milliliters of stearamidopropyldimethyl-β-hydroxylammonium nitrate 50% solution (Cyastat SN—American Cyanamid Co.); and 900 milliliters of methanol. Filter through a filter apparatus until the fluid is clean.

The formulation of Examples II and III are particularly suited for use with microbead carrier strips made of collodion.

EXAMPLE IV

Into a suitable container, place 99.9 milliliters of MIL-H-5606 hydraulic oil, and 0.1 milliliters of SHELL ASA 3 antistatic additive. Filter through a filter apparatus until the fluid is clean.

EXAMPLE V

Into a suitable container, place 99.9 milliliters of petether, and 0.1 milliliters of SHELL ASA 3 antistatic additive. Filter through a filter apparatus until the fluid is clean.

The formulations of Examples IV and V are particularly suited for use with microbead carrier strips made of paraffin.

EXAMPLE VI

The following example lists quantities sufficient for making one liter of the sixth embodiment of the invention:

Into a suitable container, place 90 milliliters of water, and 10 milliliters of Dow resin XD-7036. Filter through a filter apparatus until the fluid is clean. This formulation is particularly suited for use with microbead carrier strips made of Aerosol OT.

EXAMPLE VII

The following example lists quantities sufficient for making one liter of a seventh embodiment of the invention:

Into a suitable container place 100 milliliters of Dow Resin XD-7036; 6 milliliters of glycerol; and, 894 milliliters of distilled water. Filter through a filter apparatus until the fluid is clean and free of agglomerates. This formulation is particularly suited for use with microbead carrier strips made of polyvinyl alcohol.

In any of the formulations of Examples I through VII where it is desired to ensure against the formation of entrainment of bubbles which may interfere with the counting function, a suitable wetting agent may be added, such as iso-octyl phenoxy polyethoxy ethanol plus ethylene oxide (Triton X100-Rohm and Haas) in the amount of about 1 part per 1,000 by volume.

The hydraulic oil referred to in Example IV as "Mil-H-5606" comprises any petroleum base hydraulic fluid which conforms to the military specification identified as MIL-H-5606, issued by the U.S. Department of Defense (DOD) and available from the U.S. Printing Office as DOD publication 1971-714-159/12928. This military specification covers the general requirements of a petroleum base hydraulic fluid identified by military symbol OHA and NATO code number H515.

In each of the foregoing examples the quantity of the antistatic additive is given approximately and comprises an amount sufficient to give the coated surface of the microbeads an electrical resistivity of less than about $10^{11}$ ohms at 20° to 25° centigrade and 10% relative humidity.

From the foregoing it can be seen that there is provided by the present invention novel and improved means and methods for suppressing static charges induced on microbeads by electrokinetic or similar phenomena. The formulations given are by way of example and may be modified by those versed in the art without the exercise of invention, in accordance with the foregoing teachings.

What is claimed is:

1. An antistatic liquid media for the controlled transport of microscopic particles, the mixture comprising:
    approximately 0.1% by volume of a soluble electroconductive ionizable polymer; and
    approximately 99.9% by volume of petroleum base hydraulic oil.

2. An antistatic liquid media for the controlled transport of microscopic particles, the mixture comprising:
    approximately 0.1% by volume of a soluble ionazable antistatic agent selected from the group comprising polyvinylbenzyltrimethyl ammonium chloride, stearamidopropyldimethyl-β-hydroxyethylammonium dihydrogen phosphate, and stearamidopropyldimethyl-β-hydroxylammonium nitrate; and,
    approximately 99.9% by volume of petether.

3. An antistatic liquid media for the controlled transport of microscopic particles, the mixture comprising:
    a soluble ionizable antistatic agent selected from the group comprising polyvinylbenzyltrimethyl ammonium chloride, stearamidopropyldimethyl-β-hydroxyethylammonium dihydrogen phosphate, and stearamidopropyldimethyl-β-hydroxylammonium nitrate; a contaminant-free alcohol solvent selected from the group comprising glycerol and methanol; and,
    distilled water, the combination of said solvent and said water being in sufficient quantity to dissolve said agent.

4. The mixture defined in claim 3 including approximately one part per thousand by volume of the wetting agent comprising:
 iso-octyl phenoxy polyethoxy ethanol and ethylene oxide.

5. an antistatic media for the controlled transport of microscopic particles, the mixture comprising:
 approximately 10% by volume of polyvinylbenzyltrimethyl ammonium chloride;
 approximately 0.6% by volume of glycerol; and,
 approximately 89.4% by volume of distilled water.

6. An antistatic liquid media for the controlled transport of microscopic particles, the mixture comprising:
 approximately 10% by volume of a 35% solution of stearamidopropyldimethyl-$\beta$-hydroxyethylammonium dihydrogen phosphate; and,
 approximately 90% by volume of methanol.

7. An antistatic liquid media for the controlled transport of microscopic particles, the mixture comprising:
 approximately 10% by volume of a 50% solution of stearamidopropyldimethyl-$\beta$-hydroxylammonium nitrate; and,
 approximately 90% by volume of methanol.

* * * * *